United States Patent [19]

Shorr et al.

[11] Patent Number: 5,015,685
[45] Date of Patent: May 14, 1991

[54] PREPARATION OF TETRABROMOTETRALIN

[75] Inventors: Leonard M. Shorr, Haifa; Michael Peled, Beer-Sheva, both of Israel

[73] Assignee: Bromine Compounds Ltd., Israel, Israel

[21] Appl. No.: 482,174

[22] Filed: Feb. 20, 1990

[30] Foreign Application Priority Data

Feb. 21, 1989 [IL] Israel .......................................... 89362

[51] Int. Cl.$^5$ .......................... C08K 5/03; C07C 17/22; C07C 25/22
[52] U.S. Cl. .................................... 524/412; 521/131; 524/467; 570/183; 570/206; 570/210; 570/254
[58] Field of Search ................ 521/131; 524/412, 467; 570/183, 206, 254, 210

[56] References Cited

U.S. PATENT DOCUMENTS 3,961,033 6/1976 Kleiman et al. .................... 570/254
4,044,113 8/1977 Kleinian ............................. 570/254

OTHER PUBLICATIONS

Chemische Berichte: 54B, 597–618 (1921) Julius V. Braun.

*Primary Examiner*—Veronica P. Hoke
*Attorney, Agent, or Firm*—Michael N. Meller

[57] ABSTRACT

The novel compound 5,6,7,8-tetrabromo-1,2,3,4-tetrahydro-naphthalene (tetrabromotetralin) of the formula:

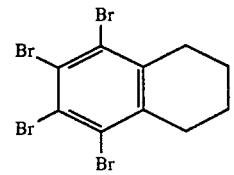

was prepared using 1,2,3,4-tetrahydro-naphthalene as the starting compound. Tetrabromotetralin was employed to prepare flame-retardant plastic compositions.

13 Claims, No Drawings

PREPARATION OF TETRABROMOTETRALIN

The present invention relates to the novel compound 5,6,7,8-tetrabromo-1,2,3,4-tetrahydro-naphthalene, referred to hereinafter as tetrabromotetralin for the sake of brevity, having the formula:

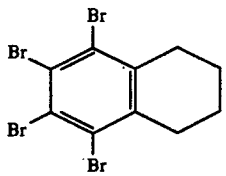

and to a process for its preparation.

Tetrabromotetralin (TBT) is a novel compound which possesses flame-retardant properties, and which can also be a useful intermediate to known compounds, such as tetrabromophthalic anhydride. While the chloro-analogue of the compound of the invention is known (Julius V. Braun, Ber. 54B, 597–618 [1921]) a similar attempt to prepare TBT only led to a mixture of monobrominated tetralins, in which the α and β isomers are found in a 66:34 ratio.

It has now been found, and this is an object of the present invention, that it is possible to provide a simple preparation method from which clean, industrially useful TBT can be prepared.

It is a further object of the invention to provide flame-retarded synthetic resins which comprise TBT as a flame-retardant agent.

Tetrabromotetralin per se is of course part of the invention, both as a novel chemical compound and as the product of the preparation method of the invention.

TBT may be used alone as an effective fire retardant, but its effectiveness is sometimes enhanced when used in conjunction with another fire retardant such as organic phosphorus compounds, chlorinated hydrocarbons such as rubbers and waxes and other organobromine compounds. Its fire retardant efficacy can be further enhanced by the use of known synergists such as the oxides, sulfides or organic salts of antimony, boron, arsenic or zinc borate. A preferred synergist for use in the compositions of this invention is antimony oxide. Also other common plastics ingredients such as fillers, pigments, lubricants, smoke suppressants, plasticisers, antioxidants etc., may be incorporated.

The process for the preparation of TBT according to the invention comprises brominating purified 1,2,3,4-tetrahydro-naphthalene (Tetralin) in an organic solvent in the presence of a catalytically effective amount of a bromination catalyst. It should be emphasized that the purity of the Tetralin employed as the starting material is very important. If no purification of the Tetralin is effected, and the material employed contains impurities, specifically peroxides and/or hydroperoxides, a black product is obtained which cannot be used. Tetralin readily oxidizes to form peroxidic materials and the commercial material often is contaminiated thereby. If these contaminants are not removed prior to bromination, a black product is obtained which cannot be used. Removal of such impurities can be achieved by acid destruction, extraction with aqueous base, distillation, absorption on active absorbants such as alumina and silica, or combinations of these treatments.

The organic solvent employed in the reaction must be a solvent in which Tetralin is soluble, and is preferably inert under the conditions of the reaction. Preferred solvents for this purpose are, e.g., methylene dichloride and ethylene dichloride.

As will be apparent to a person skilled in the art, the highest practical reaction temperature depends upon the solvent employed, and does not exceed the boiling point of the solvent. The lowest possible temperature, on the other hand, depends on the catalyst employed. It is not uncommon to operate at temperatures as low as 0° C., so that it will be appreciated that a wide temperature range can be employed in the process of the invention.

The preferred bromination catalyst for the reaction is aluminum chloride. However, other suitable catalysts will be recognized by the skilled chemist. Likewise, the preferred bromination agent is bromine, but other effective brominating agents, such as BrCl, can be employed.

The above and other characteristics and advantages of the invention will be illustrated by the following non-limitative examples.

EXAMPLE 1

Preparation of Tetrabromotetralin (A) Impurities Wash

Tetralin is thoroughly washed several times, e.g., with concentrated $H_2SO_4$, in order to remove impurities. Removal of impurities is of paramount importance for obtaining a pure product. However, if Tetralin which has been previously purified is used, or high-grade Tetralin obtained from any other source, then of course this step can be dispensed with.

(B) Bromination

To a 1 liter three-necked flask equipped with mechanical stirrer, cooling sleeve and funnel, there are added 79 gr. (0.6 moles) of purified Tetralin from step A, 500 ml methylene dichloride and 2 gr. aluminum chloride as a catalyst. To this mixture there are added dropwise 420 gr. (2.6 moles) of bromine during about one hour. HBr evolves throughout the reaction. After completion of these operations, the resulting mixture is stirred for an additional one hour.

The reaction is carried out at reflux. At the end of the reaction the mixture is cooled, bleached with ammonia or bisulfite, neutralized with a 10% diluted carbonate solution, filtered and washed with water. The solvent is then evaporated, and 214 gr. of a solid product is obtained, having a melting point of 180° C. The yield is 80% with respect to Tetralin.

The solid is recrystallized from ethyl acetate, to provide a white to off white solid with a m.p. of 184°–186° C., which is soluble in chloroform, and is not soluble in alcohols, acetone, acetonitrile or petrol ether 60–80. Recrystallization can likewise be carried out using THF, dioxane, toluene, xylene, etc.

N.M.R. (CDCl$_3$): 1.8 (M, 4H), 2.7 (M, 4H).

I.R. (KBr): 830, 950, 1300, 1360, 1420, 2900.

Br %—calculated: 71.4, found: 72.2.

Sublimation point: 160° C./1 mmHg.

EXAMPLE 2

Flame-Retardant Activity

A flame-retarded High-Impact Polystyrene resin (HIPS) was prepared, using TBT prepared according to Example 1.

The composition contained, on a weight basis, 27.9% TBT, 7.3% antimony trioxide (ex Campine), 63.8% HIPS Galirene Q-88-5 (ex IPE), 0.5% Tinuvin P (ex Ciba-Geigy) and 0.5% Calcium Stearate (ex WITCO). The final bromine content was 20.1%.

The composition so obtained was tested in the UL-94 standard test (1.6 mm), and was found to be VO according to the UL-94 rating.

EXAMPLE 3

TBT as Fire Retardant in Unsaturated Polyester 1.2 Parts of TBT were mixed into 15 parts of Fiberplast 555 (an unsaturated polyester resin, Fiberplast Ltd., Haifa). The mixture was cured for five hours at ambient temperature followed by five hours at 80 degrees C. after adding 0.15 parts MEK peroxide and 0.1 part cobalt octoate solution. The product had a bromine content of 6 phr and a Limiting Oxygen Index of 21.7 compared to 18.8 for the same resin cured similarly but in the absence of TBT.

EXAMPLE 4

TBT as Fire Retardant in a Polyurethane Foam

A sorbitol-based polyether polyol (37.2 g) having a hydroxyl number of 490 mg KOH/g was mixed with 10.0 g. TBT, 15.8 g. Santicizer 141 (an alkaryl phosphate produced by Monsanto), 0.25 g. water, 1.0 g. of a silicone surfactant and 1.0 g. of dimethylcyclohexylamine as catalyst. When homogeneous, 15.0 g. of Freon 11 were added and the mixture stirred vigorously for 45 seconds. Diphenylmethane diisocyanate (MDI, 51.2 g.) was then added and stirring was continued for five seconds more. The mixture was poured into a cardboard box lined with wrapping paper and left to rise freely. The cream time (measured from the moment of MDI introduction) was 38 seconds and the rise time was 290 seconds. A similar foam was prepared but without added fire retardants.

The fire retarded foam was found to have a Limiting Oxygen Index of 23.3 versus 18.6 for the blank.

The above examples of preparation and compositions have been provided for the purpose of illustration, and are not intended to be limitative. Many variations can be effected in the process for the preparation of TBT, and many different flame-retarded plastic compositions embodying TBT can be prepared, with different resins, additives and proportions, all without exceeding the scope of the invention.

We claim:

1. The compound 5,6,7,8-tetrabromo-1,2,3,4-tetrahydro-naphthalene of the formula:

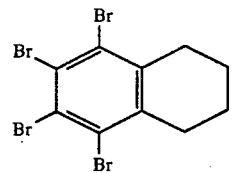

2. A process for preparing 5,6,7,8-tetrabromo-1,2,3,4-tetrahydro-naphthalene, comprising the steps of:
   (a) providing purified 1,2,3,4-tetrahydro-naphthalene by removing peroxides and/or hydroperoxides; and
   (b) brominating the said purified 1,2,3,4-tetrahydro-naphthalene with a bromination agent in an organic solvent in the presence of a catalytically effective amount of a bromination catalyst.

3. A process as in claim 2, wherein the bromination agent is bromine.

4. A process as in claim 3, wherein the bromination catalyst is aluminum chloride.

5. A process as in claim 2, which the organic solvent is selected from the group consisting of methylene dichloride and ethylene dichloride.

6. A flame-retarded plastic composition comprising as an active ingredient 5,6,7,8-tetrabromo-1,2,3,4-tetrahydro-naphthalene, alone or together with other fire retardant or synergistic materials or both.

7. A composition as in claim 6, wherein the plastic material is selected from among high impact polystyrene, unsaturated polyester or polyurethane foam.

8. A composition as in claim 6, comprising one or more organic phosphorus compounds as a flame retardant.

9. A composition as in claim 6, comprising antimony oxide as a fire retardant synergist.

10. A composition as in claim 7, comprising one or more organic phosphorus compounds as a flame retardant.

11. A composition as in claim 7, comprising antimony oxide as a fire retardant synergist.

12. A composition as in claim 8, comprising antimony oxide as a fire retardant synergist.

13. A method for rendering flammable plastic materials flame retardant, comprising admixing said flammable material with a flame-retarding effective amount of 5,6,7,8-tetrabromo-1,2,3,4-tetrahydro-naphthalene.

* * * * *